(12) United States Patent
Wang

(10) Patent No.: US 8,419,429 B2
(45) Date of Patent: Apr. 16, 2013

(54) IMPLANT PROSTHETIC PART SET AND METHOD OF MANUFACTURING REPLICATION PLASTER MODEL INCLUDING ABUTMENT USING THE SAME

(75) Inventor: Je-Won Wang, Daejeon-si (KR)

(73) Assignee: Innobiosurg Corporation, Daejeon-si (KR)

( * ) Notice: Subject to any disclaimer, the term of this patent is extended or adjusted under 35 U.S.C. 154(b) by 0 days.

(21) Appl. No.: 13/254,215

(22) PCT Filed: Mar. 10, 2010

(86) PCT No.: PCT/KR2010/001477
§ 371 (c)(1),
(2), (4) Date: Sep. 1, 2011

(87) PCT Pub. No.: WO2010/110541
PCT Pub. Date: Sep. 30, 2010

(65) Prior Publication Data
US 2011/0318711 A1  Dec. 29, 2011

(30) Foreign Application Priority Data
Mar. 23, 2009 (KR) .......... 10-2009-0024632

(51) Int. Cl.
*A61C 5/08* (2006.01)

(52) U.S. Cl.
USPC ............................ 433/173; 433/214

(58) Field of Classification Search .......... 433/172, 433/173, 174, 214, 215
See application file for complete search history.

(56) References Cited

U.S. PATENT DOCUMENTS

| | | | |
|---|---|---|---|
| 5,904,483 A | | 5/1999 | Wade |
| 6,227,856 B1 * | | 5/2001 | Beaty et al. ............. 433/172 |
| 6,358,050 B1 * | | 3/2002 | Bergstrom et al. ....... 433/173 |
| 6,488,501 B1 * | | 12/2002 | Harding .................. 433/173 |
| 6,508,650 B2 * | | 1/2003 | Gittleman ............... 433/172 |
| 6,951,460 B2 * | | 10/2005 | Halldin et al. ........... 433/173 |
| 7,632,096 B2 * | | 12/2009 | Gittleman ............... 433/173 |
| 7,654,824 B2 * | | 2/2010 | Ebi et al. ................. 433/214 |

FOREIGN PATENT DOCUMENTS

KR  10-0841218 B1  6/2008

* cited by examiner

*Primary Examiner* — Ralph Lewis
(74) *Attorney, Agent, or Firm* — Sherr & Jiang, PLLC

(57) ABSTRACT

Provided are an implant prosthetic part set and a method of manufacturing replication plaster model including an abutment using the same, which can take an impression of the location and the shape of a fixture in an oral cavity without using a typical impression copping, in order to manufacture an upper prosthesis coupled to the fixture implanted into an alveolar bone.

4 Claims, 4 Drawing Sheets

IMPLANT PROSTHETIC PART SET AND METHOD OF MANUFACTURING REPLICATION PLASTER MODEL INCLUDING ABUTMENT USING THE SAME

TECHNICAL FIELD

The present invention relates to an implant prosthetic part set and a method of manufacturing replication plaster model including an abutment using the same, which can take an impression of the location and the shape of a fixture in an oral cavity without using a typical impression copping, in order to manufacture an upper prosthesis coupled to the fixture implanted into an alveolar bone.

BACKGROUND ART

In dentistry, implants mean implanting an artificial tooth into a dental bone. A dental root formed of titanium is implanted into an alveolar bone, and then an artificial tooth is fixed thereon to recover the function of the original tooth.

In the case of general prostheses and dentures, surrounding teeth or bones are damaged over time, but in the case of implants, peripheral dental tissues are not damaged, and no caries arise while having the same function and shape as natural teeth. Accordingly, the implants can be used semi-permanently.

Also, implants may facilitate the recovery of a single missing tooth and improve the function of an artificial tooth for a partially or completely edentulous patient, and may improve dental prosthesis recovery in terms of aesthetic. Furthermore, implants disperse an excessive stress applied on tissues of a support bone thereunder.

Implants include a surgery operation which implants a fixture into a gingival bone, i.e., an alveolar bone, and a prosthetic operation which mounts an artificial tooth by connecting an abutment to the fixture.

An example of the prosthetic operation will be described below. In a typical prosthetic surgery, a fixture is implanted into an alveolar bone, and after a certain period (about three to six months) for osseointegration, an impression copping is screwed into a hole of an upper portion of the fixture. Thereafter, an impression copping fixing screw (guide screw) is inserted into an upper portion of the impression copping to secure the impression copping and the fixture, and then surrounding teeth and the above-described parts are coated with an impression material. The impression copping fixing screw projecting from the impression material is then unscrewed to obtain an impression in which the impression copping separated from the fixture is fixed. Thereafter, the impression copping in the impression is coupled with a virtual fixture (analog), and is fixed with the impression copping fixing screw. Thereafter, plaster is filled in the impression to be hardened, and then the impression copping fixing screw is unscrewed to remove the impression and the impression copping, remaining a plaster model. Thereafter, an abutment is coupled to the plaster model, and a crown (artificial tooth) is formed on the abutment. However, there is a limitation in that since the impression is primarily formed on the upper portion of the fixture within a certain period after the implantation of the fixture into the alveolar bone, the analog is twice coupled to the impression copping and the abutment, resulting in poor bonding due to abrasion of the analog. Also, the prosthetic surgery is not economical because the disposable impression copping used in the surgery should be discarded.

Korean Patent Publication No. 10-2009-0014027 discloses a dental implant material including a silver or silver alloy layer with a nanometer or micrometer thickness formed on at least a portion of the surface of the dental implant material. Thus, an abutment screw of the dental implant material is improved in a unscrew protection function, and can show an anti-bacterial effect that can prevent bacterial infection. Also, an abutment of the dental implant material can show an anti-bacterial effect that can prevent bacterial infection, and can prevent peri-implantitis.

Korean Patent Registration No. 10-0671710 discloses an implant driver with a free angle, including a power combination unit for mounting a handle or a handpiece to a power shaft delivering a rotation force; a rotation force delivering unit delivering the rotation force to a work shaft of a driver; a driver performing a work on the work shaft; and a path guiding unit for guiding from the power shaft to the work shaft.

Korean Patent Registration No. 10-0842096 discloses a block body becoming an abutment, an upper artificial tooth structure, or a complex body of the abutment and the upper artificial tooth structure through machining, and including a connection part that prevents rotation upon combination with a fixture or a dental prosthesis on one side thereof, in which a connection structure is formed in a dental implant abutment and an upper structure.

DISCLOSURE

Technical Problem

Conventionally, in order to take an impression of the location and the shape of a fixture implanted into an alveolar bone in an oral cavity of a patient, an impression copping (4) of FIG. 4 has been used, and in order to manufacture an implant crown, the following processes have been performed to manufacture a plaster model in which an abutment is combined at the same place as the oral cavity of a patient.

(1) At Dentist's Office

① An impression copping (4) is inserted in an upper portion of a fixture (not shown). A guide screw (5) is then downwardly screwed into the fixture through a central hole of the impression copping (4).

② An impression material is filled in an impression tray having holes allowing the guide screw to be exposed. The impression copping, surrounding teeth, and oral soft tissues are covered with the impression tray to be coated with impression material.

③ When impression material is hardened, the guide screw exposed over the tray is unscrewed to release a screw coupling between the fixture and the impression copping.

④ The impression tray including the impression copping in accordance with the shape of the surrounding teeth and the fixture is removed from the oral cavity of a patient to be sent to a prosthetic dental laboratory.

(2) At Dental Laboratory

⑤ An analog (a dental duplication fixture) is aligned with the impression copping fixed in the impression material of the impression tray. The guide screw is screwed through the central hole of the impression copping to fix the analog to the lower portion of the impression copping.

⑥ Plaster is filled in a negative mold formed of the impression material and is then hardened.

⑦ After the plaster is hardened, the guide screw is unscrewed to release the coupling of the analog and the impression copping, and the impression material included in the impression copping is removed from the hardened plaster model.

⑧ An abutment (3) is inserted into the plaster model in which the analog is uprightly implanted in accordance with the condition of the oral cavity of a patient, and the abutment is fixed to the plaster model by an abutment fixing screw (1) to complete the plaster model.

⑨ An implant crown is manufactured on the abutment of the completed plaster model.

As described above, the process in the dental laboratory is complex or error-prone. Also, there is an economic limitation in that the impression copping has to be disposably used.

Selection of the abutment at the dental laboratory is less matched with implant-surrounding tissues than direct selection in the oral cavity.

Accordingly, the present invention provides an implant prosthetic part set and a method of manufacturing replication plaster model including an abutment using the same, which prevents an error generated from deformation of the combination shape (hex screw) of an impression copping with a fixture when the impression copping is reused through sterilization and disinfection.

Technical Solution

In one general aspect, an implant prosthetic part set includes: an abutment adapted to be inserted into an upper portion of a fixture adapted to be implanted into an alveolar bone; an impression attachment part screwed into an upper portion of the abutment; and an abutment fixing screw for fixing a combination body of the abutment and the impression attachment part to the fixture, wherein: the abutment has a cylindrical shape and a through hole vertically passing therethrough and has a female screw thread on an inner circumferential surface of an upper end portion thereof; a diameter of the abutment becomes narrower as getting closer to a lower end portion thereof; and the lower end portion thereof has a hexagonal shape.

Other features and aspects will be apparent from the following detailed description, the drawings, and the claims.

Advantageous Effects

Since the present invention does not use an impression copping, it is economic. Also, since a plaster model is manufactured in a state where an abutment is mounted, the plaster model can be more exactly manufactured, and the dental laboratory work is simpler. In addition, since an appropriate abutment can be selected in the oral cavity of a patient, it is possible to manufacture an upper prosthesis that further matches an actual oral cavity, and solve a reduction of accuracy generated from repetitive use of the impression copping.

BEST MODE

Figure 1:
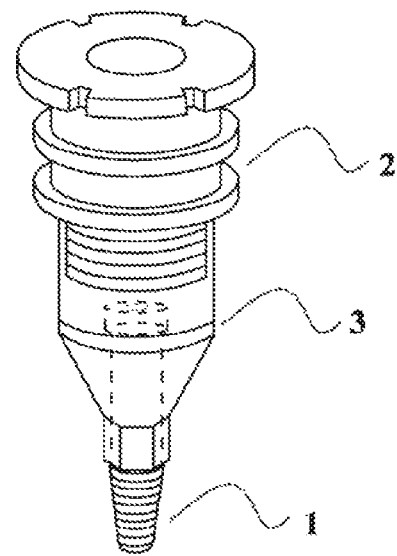
FIG. 1 is a view illustrating an implant prosthesis set according to an embodiment of the present invention.

Hereinafter, exemplary embodiments will be described in detail with reference to the accompanying drawings.

EXAMPLE

A fixture is implanted into an alveolar bone of a patient. After a certain period (about 3 months to about 6 months) for osseointegration of the fixture, a replication plaster model for dental laboratory may be manufactured to have the same shape as the surrounding shape of the position where the fixture is implanted in the oral cavity to manufacture an upper prosthesis (artificial tooth).

For this, at a dentist's office, a complex body of an impression material combination part and an abutment fit for the fixture and matching the oral environment may be inserted into the fixture. A hex driver (such as a head hole of an abutment fixing screw) may be loaded in the central hole of the complex body, and then the abutment fixing screw may be fastened to fix the complex body and the fixture (here, the hex driver is left intact).

Impression material may be loaded in an impression tray having a hole that can expose the impression material using the hex driver. The impression tray may cover the complex body and parts including surrounding teeth and oral tissues, and impression material may be coated thereon.

When the impression material is hardened, the abutment fixing screw fastened on the fixture may be unscrewed using the hex driver. The tray including the impression material with the complex body may be carefully removed from the oral cavity (here, the inside of the tray may have a negative mold according to the lower portion of the abutment coupled to the fixture, surrounding teeth, and surrounding tissues).

At a dental laboratory, an analog (replication fixture for dental laboratory work, having the same shape as the fixture, hereinafter, referred to as analog) may be fitted to the lower portion of the complex body of abutment and impression attachment part buried in the impression material. The analog and the lower portion of the abutment may be fixed by an abutment fixing screw, and then plaster may be poured into the inner surface of the impression tray and be hardened. Thereafter, the impression material may be removed, and then the impression attachment part may be turned to be removed from the abutment. Thus, a plaster model in which the abutment is connected in the oral cavity may be manufactured.

An artificial crown may be formed on the abutment of the plaster model. When the artificial crown (upper prosthesis) is manufactured, the abutment and the artificial crown (upper prosthesis) may be removed from the plaster model for dental laboratory work, and may be fixed on the fixture in the oral cavity of a patient. The plaster model for dental laboratory work, in which the analog is implanted, may be discarded.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

MODE FOR INVENTION

In order to achieve the above purposes, the present invention relates to an implant prosthetic part set and a method of manufacturing replication plaster model including an abutment using the same, which can take an impression of the location and the shape of a fixture in an oral cavity without using a typical impression copping, in order to manufacture an upper prosthesis coupled to the fixture implanted into an alveolar bone.

Hereinafter, exemplary embodiments of the present invention will be described in detail with reference to the accompanying drawings.

Figure 2:
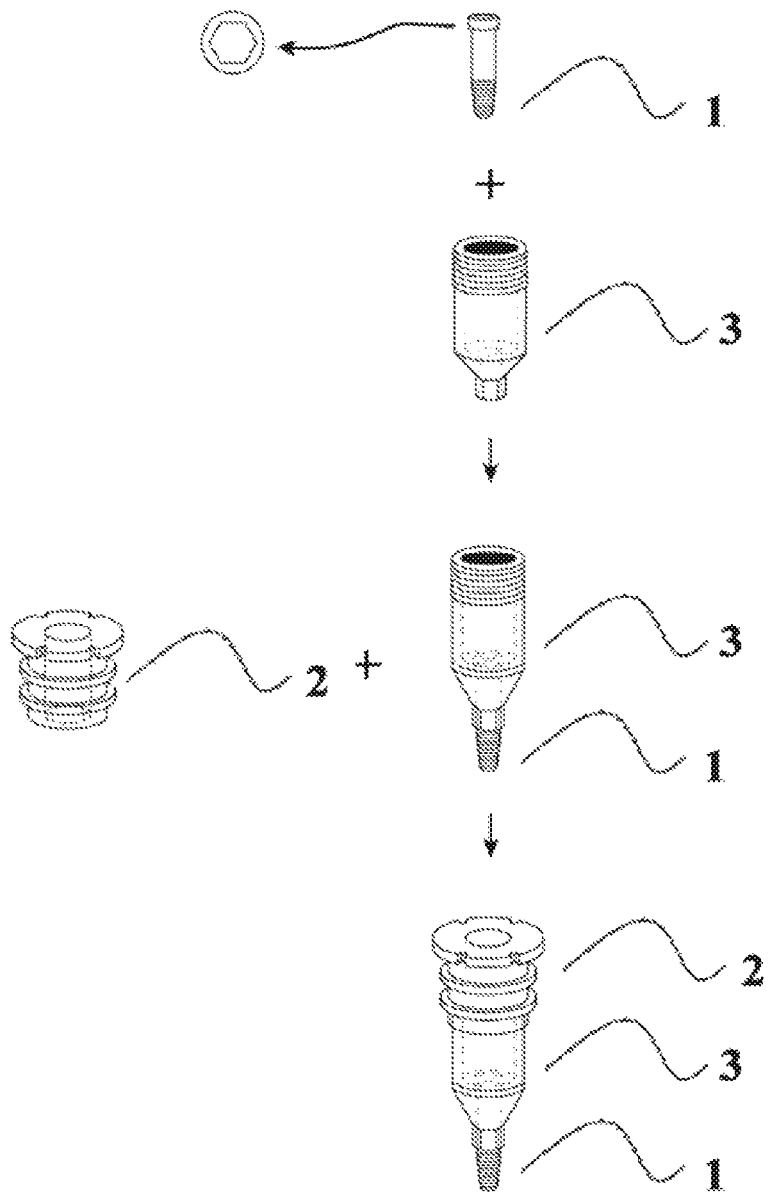
FIG. 2 is an exploded view illustrating an exemplary implant prosthesis set according to an embodiment of the present invention.
Figure 3:
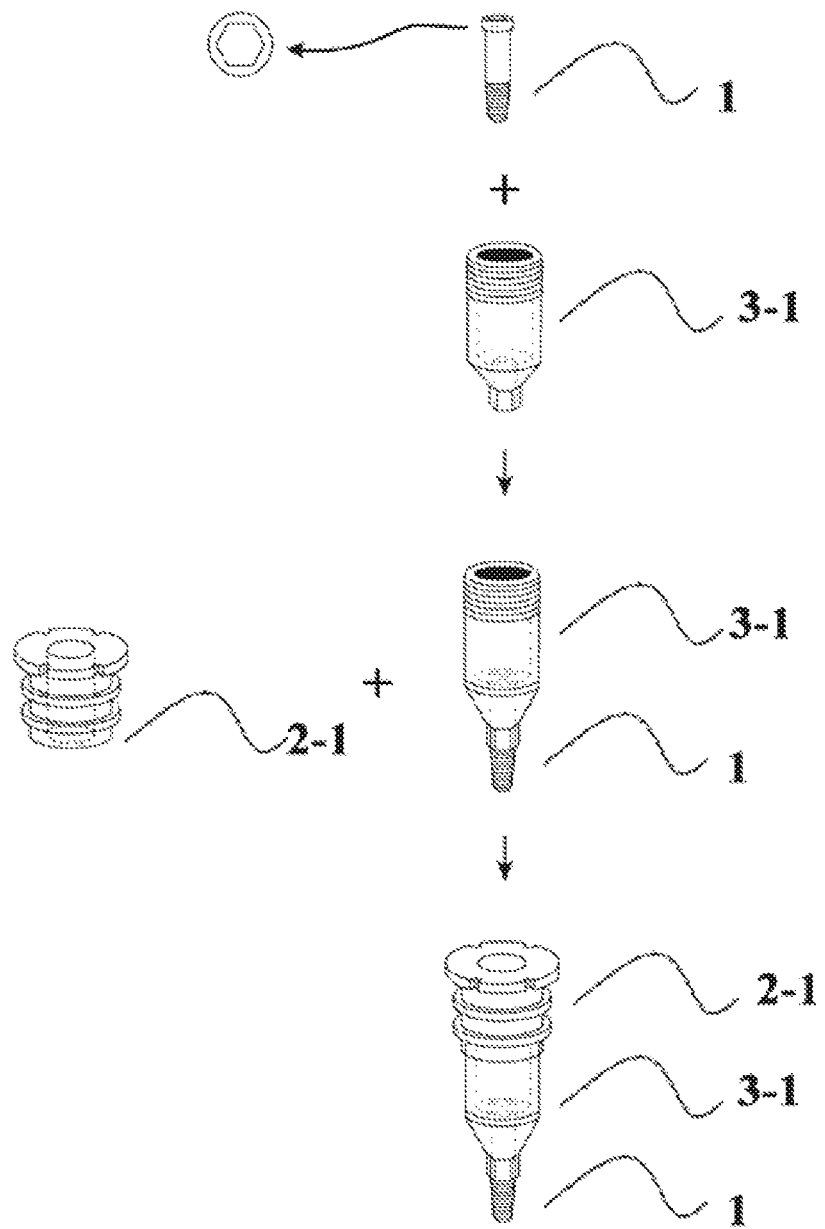
FIG. 3 is a view illustrating another exemplary implant prosthesis set according to an embodiment of the present invention.
Figure 4:
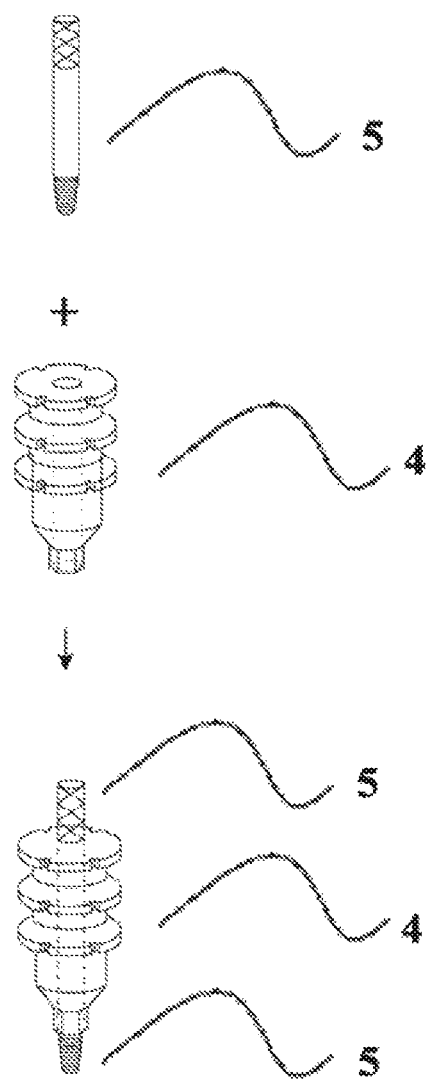
FIG. 4 is a view illustrating a conventional implant prosthesis set.

FIG. 1 is a view illustrating an implant prosthesis set according to an embodiment of the present invention. FIG. 2 is an exploded view illustrating an exemplary implant prosthesis set according to an embodiment of the present invention. FIG. 3 is a view illustrating another exemplary implant prosthesis set according to an embodiment of the present invention. FIG. 4 is a view illustrating a conventional implant prosthesis set. There are shown an abutment fixing screw 1, an impression attachment part 2 and 2-1, an abutment 3 and 3-1, an impression copping fixing screw (guide screw) 5, and an impression copping 4.

To explain the structure, as shown in FIGS. 1 and 2, the implant prosthetic part set may include an abutment 3 and 3-1 inserted into an upper portion of a fixture implanted into an alveolar bone, an impression attachment screwed into an upper portion of the abutment 3 and 3-1, and an abutment fixing screw 1 for fixing a combination body of the abutment 3 and 3-1 and the impression attachment part 2 and 2-1 to the fixture.

The abutment 3 may be formed to have a cylindrical shape and a through hole vertically passing therethrough. The abutment 3 may have a female screw thread on the inner circumferential surface of the upper end thereof. The diameter of the abutment 3 may be narrowed as it gets closer to a lower end thereof. The lower end of the abutment 3 may have a hexagonal screw shape.

The impression attachment part 2 may be screwed into the through hole of the abutment 3, and may have a male screw thread on the outer circumferential surface of the lower end thereof. The impression attachment part 2 may have a plurality of flanges and a plurality of holes in the edges of each flange to prevent impression material from being separated from the impression attachment part 2 when taking an impression using impression material. The plurality of flanges may be spaced from each other by a certain distance.

As shown in FIG. 2, the abutment fixing screw 1 may have a hexagonal hole in the upper portion thereof, and may have a male screw thread engaging with the female screw thread in the inside of the fixture.

As shown in FIG. 2, the head of the abutment fixing screw 1 may have a hexagonal hole when viewed from top.

FIG. 3 illustrates another combination of an abutment and an impression attachment part. An abutment 3-1 may have a male screw thread on the outer circumferential surface of the upper portion thereof instead of the female screw thread on the inner circumferential surface of the upper portion of the abutment 3. An impression attachment part 2-1 may have a female screw thread on the inner circumferential surface of the lower portion thereof instead of the male screw thread on the outer circumferential of the lower portion of the impression attachment part 2.

More specifically, the abutment 3-1 may have a cylindrical shape, and may have a through hole vertically passing therethrough. The diameter of the abutment 3-1 may be narrowed as it gets closer to the end portion thereof. The end portion of the abutment 3 may have a hexagonal screw shape. The abutment 3-1 may have a male screw thread on the outer circumferential surface of the upper portion thereof.

The impression attachment part 2-1 may be formed to have a through hole vertically passing therethrough, and may have a female screw thread on the inner circumferential surface of the end portion thereof.

The impression attachment part 2-1 may include a plurality of flanges and a plurality of holes in edges of each flange to facilitate removal of an impression when taking the impression using impression material. The plurality of flanges may be spaced from each other by a certain distance.

INDUSTRIAL APPLICABILITY

The present invention relates to an implant prosthetic part set and a method of manufacturing replication plaster model including an abutment using the same, which uses a complex body of an abutment and an impression attachment part without using an impression copping.

The invention claimed is:

1. An implant prosthetic part set comprising:
   an abutment adapted to be inserted into an upper portion of a fixture adapted to be implanted into an alveolar bone;
   an impression attachment part screwed into an upper portion of the abutment; and
   an abutment fixing screw for fixing a combination body of the abutment and the impression attachment part to the fixture,
   wherein:
   the abutment has a cylindrical shape and a through hole vertically passing therethrough and has a female screw thread on an inner circumferential surface of an upper end portion thereof;
   a diameter of the abutment becomes narrower as getting closer to the upper a lower end portion thereof; and
   the lower end portion thereof has a hexagonal shape,
   wherein the impression attachment part has external threads that mate with the female threads of the abutment.

2. The implant prosthetic part set of claim 1, wherein the impression attachment part is formed to have a through hole vertically passing therethrough, wherein the external threads of the impression attachment part is a male screw thread on an outer circumferential surface of a lower end portion of the impression attachment part, and the impression attachment part comprises a plurality of flanges spaced from each other by a certain distance to prevent impression from being separated from the impression attachment part, each of the flanges having a plurality of holes on edges thereof.

3. An implant prosthetic part set comprising:
   an abutment adapted to be inserted into an upper portion of a fixture adapted to be implanted into an alveolar bone;
   an impression attachment part screwed into an upper portion of the abutment; and
   an abutment fixing screw for fixing a combination body of the abutment and the impression attachment part to the fixture,
   wherein:
   the abutment is formed to have a cylindrical shape and a through hole vertically passing therethrough;
   the diameter of the abutment becomes narrower as getting closer to an end portion thereof;
   the abutment has a hexagonal screw shape at the end portion thereof and a male screw thread on an outer circumferential surface of the upper portion thereof;
   the impression attachment part is formed to have a through hole vertically passing therethrough and a female screw thread on an inner circumferential surface of an end portion thereof; and the impression attachment part comprises a plurality of flanges spaced from each other by a certain distance to prevent impression from being separated from the impression attachment part, each of the flanges having a plurality of holes on edges thereof.

4. A method for manufacturing a replication plaster model comprising an abutment using an implant prosthetic part set, the method comprising:

inserting a complex body of an abutment and an impression combination part, matching a fixture in an alveolar bone, into the fixture to secure the complex body and the fixture by putting a hex driver into a central through hole of the complex body and fastening an abutment fixing screw;

loading impression material in an impression tray having holes exposed to a hex driver, covering the complex body and surrounding teeth and oral tissues with the impression tray to be coated with the impression material, and then when the impression material is hardened, and unscrewing an abutment fixing screw fastened to the fixture using the hex driver to remove the impression tray comprising the impression material with the complex body from an oral cavity; and inserting an analog into a lower portion of the complex body of the abutment and the impression attachment part buried in the impression material, fixing the analog and the lower portion of the abutment with an abutment fixing screw, pouring plaster into the inner surface of the impression tray to harden, removing the impression material, and unscrewing the impression attachment part to remove the impression attachment part from the abutment and thus manufacture the plaster model in which the abutment is connected in the oral cavity.

* * * * *